(12) United States Patent
Kagami et al.

(10) Patent No.: US 12,127,634 B2
(45) Date of Patent: Oct. 29, 2024

(54) FOOT LENGTH INFORMATION MANAGEMENT SYSTEM, SYSTEM FOR DETERMINING REPLACEMENT TIME FOR SHOES, AND MEASUREMENT ASSISTING TOOL

(71) Applicant: ASICS Corporation, Hyogo (JP)

(72) Inventors: Kana Kagami, Hyogo (JP); Norihiko Taniguchi, Hyogo (JP)

(73) Assignee: ASICS Corporation, Hyogo (JP)

( * ) Notice: Subject to any disclaimer, the term of this patent is extended or adjusted under 35 U.S.C. 154(b) by 465 days.

(21) Appl. No.: 17/500,611

(22) Filed: Oct. 13, 2021

(65) Prior Publication Data

US 2022/0095748 A1 Mar. 31, 2022

Related U.S. Application Data

(62) Division of application No. 16/954,986, filed as application No. PCT/JP2019/050785 on Dec. 25, 2019, now Pat. No. 11,419,390.

(51) Int. Cl.
*A61B 5/107* (2006.01)
*A43D 1/02* (2006.01)
(Continued)

(52) U.S. Cl.
CPC ............. *A43D 1/025* (2013.01); *A61B 5/107* (2013.01); *G01B 3/02* (2013.01); *G06Q 30/06* (2013.01);
(Continued)

(58) Field of Classification Search
CPC ........ A61B 5/107; A61B 5/1074; A61B 5/103
(Continued)

(56) References Cited

U.S. PATENT DOCUMENTS 226,429 A * 4/1880 Varnum .................. A43D 1/02
33/3 A
2,775,037 A * 12/1956 Baumunk .............. G01B 3/566
33/499
(Continued)

FOREIGN PATENT DOCUMENTS

DE  10 2011 121 086 A1  6/2013
FR      3060735 A1       6/2018
(Continued)

OTHER PUBLICATIONS

Extended European Search Report issued in corresponding European Patent Application No. 19894395.3, dated Aug. 23, 2021.
(Continued)

*Primary Examiner* — George B Bennett
(74) *Attorney, Agent, or Firm* — Rimon P.C.

(57) ABSTRACT

A system for managing foot length information of a growing person is to be provided. A foot length information management system includes: a measurement unit that measures foot length; a storage unit that stores multiple patterns of growth curve information; an age information input unit into which age information of a customer is entered; and a growth curve information selecting unit that refers to the age information to select growth curve information corresponding to foot length measured by the measurement unit, from among the multiple patterns of growth curve information. The foot length information management system may further include a recording unit in which past foot length is recorded, and the growth curve information selecting unit may select growth curve information based on foot length recorded in the recording unit and foot length measured by the measurement unit.

3 Claims, 5 Drawing Sheets

(51) Int. Cl.
  *G01B 3/02* (2020.01)
  *G06Q 30/06* (2023.01)
  *G06Q 30/0601* (2023.01)
(52) U.S. Cl.
  CPC ..... *G06Q 30/0623* (2013.01); *G06Q 30/0631* (2013.01)
(58) Field of Classification Search
  USPC .......... 33/3 A, 3 R, 483, 484, 485, 452, 465, 33/511, 512
  See application file for complete search history.

(56) References Cited

U.S. PATENT DOCUMENTS

| | | | | |
|---|---|---|---|---|
| 4,939,849 | A * | 7/1990 | Johnson | G01B 5/02 33/712 |
| 5,020,233 | A * | 6/1991 | Syken | B43L 7/12 33/456 |
| 6,643,942 | B1 * | 11/2003 | Russell | G01C 9/28 33/459 |
| 6,983,548 | B1 * | 1/2006 | Cook | A43D 1/02 33/515 |
| 7,200,951 | B2 * | 4/2007 | O'Connor | H02G 1/00 33/528 |
| 7,469,480 | B2 * | 12/2008 | Nottingham | G01C 15/002 362/89 |
| 7,841,098 | B2 * | 11/2010 | Richter | G01B 5/061 600/587 |
| 8,375,592 | B1 * | 2/2013 | Holt | B43L 7/14 33/456 |
| 8,539,690 | B2 * | 9/2013 | Haykeen | A61B 5/1072 600/587 |
| 8,782,914 | B1 * | 7/2014 | DeLuca | G01B 3/06 33/458 |
| 8,887,402 | B2 * | 11/2014 | Doppel | A61B 5/1072 33/2 A |
| 8,966,776 | B2 * | 3/2015 | Kelly | G01C 15/12 33/286 |
| 9,019,359 | B2 | 4/2015 | Leedy et al. | |
| 9,351,666 | B2 * | 5/2016 | Wojcieszak | A43D 1/02 |
| 10,772,536 | B2 * | 9/2020 | Mathiasmeier | A61B 5/1074 |
| 11,733,017 | B2 * | 8/2023 | Weskamp | G01B 3/08 33/511 |
| 2002/0157270 | A1 * | 10/2002 | Maraschiello | A63B 60/42 33/484 |
| 2003/0033723 | A1 * | 2/2003 | Snook | A61B 5/1074 33/515 |
| 2009/0094138 | A1 | 4/2009 | Sweitzer et al. | |
| 2013/0167391 | A1 * | 7/2013 | Pratinidhi | A61B 5/1074 33/512 |
| 2016/0081435 | A1 | 3/2016 | Marks | |
| 2017/0086751 | A1 * | 3/2017 | Amos | A61B 5/4528 |
| 2018/0035762 | A1 * | 2/2018 | Towns | G06T 7/001 |
| 2023/0408238 | A1 * | 12/2023 | Ray | G01B 3/20 |

FOREIGN PATENT DOCUMENTS

| | | |
|---|---|---|
| JP | 2004-220152 A | 8/2004 |
| JP | 2007-265077 A | 10/2007 |

OTHER PUBLICATIONS

Liu, Ying, "Research and Implementation of Children's Wear Model Based on Improved BP Algorithm," Oct. 1, 2019, 2019 3rd International Conference on Electronic Information Technology and Computer Engineering, pp. 1346-1350 (Year: 2019).
Non-Final Rejection issued in corresponding U.S. Appl. No. 16/954,986, dated Nov. 18, 2021.
International Search Report issued for the corresponding PCT Application No. PCT/JP2019/050785, dated Mar. 24, 2020, with English translation.
European Office Action issued in corresponding European Patent Application No. 19 894 395.3, dated Aug. 29, 2023.

* cited by examiner

FOOT LENGTH INFORMATION MANAGEMENT SYSTEM, SYSTEM FOR DETERMINING REPLACEMENT TIME FOR SHOES, AND MEASUREMENT ASSISTING TOOL

CROSS REFERENCE TO RELATED APPLICATION

This patent application is the divisional of U.S. application Ser. No. 16/954,986, filed Jun. 17, 2020, which is the U.S. National Phase under 35 U.S.C. § 371 of International Application No. PCT/JP2019/050785, filed on Dec. 25, 2019, the entire contents of which are hereby incorporated by reference in its entirety.

TECHNICAL FIELD

The present invention relates to a foot length information management system, a system for determining a replacement time for shoes, and measurement assisting tools.

BACKGROUND ART

Various technologies for measuring foot length have been conventionally proposed (Patent Literature 1, for example). However, information obtained in measurement is merely used temporarily when shoes are purchased, for example, and is in fact not used effectively.

PRIOR ART REFERENCE

Patent Literature

[Patent Literature 1] U.S. Pat. No. 9,019,359

For example, the foot length of a child changes as the child grows up, and new shoes need to be purchased regularly with the growth of the child. However, since the child cannot subjectively judge if the shoes fit his or her feet, a guardian of the child needs to regularly check how the shoes fit the child's feet. Therefore, there are a certain amount of demands for managing foot length information of growing children with their growth.

SUMMARY OF INVENTION

Technical Problem

The present invention has been made based on the demands above, and a purpose thereof is to provide a system for managing foot length information of a growing person.

Solution to Problem

To solve the problem above, one embodiment of the present invention includes: a measurement unit that measures foot length; a growth curve information storage unit that stores multiple patterns of growth curve information; an age information input unit into which age information of a customer is entered; and a growth curve information selecting unit that refers to the age information to select growth curve information corresponding to foot length measured by the measurement unit, from among the multiple patterns of growth curve information.

BRIEF DESCRIPTION OF DRAWINGS

Embodiments will now be described, by way of example only, with reference to the accompanying drawings which are meant to be exemplary, not limiting, and wherein like elements are numbered alike in several Figures, in which.

DESCRIPTION OF EMBODIMENTS

In the following, a foot length information management system 10 according to an embodiment will be described. The foot length information management system 10 is a system used in a shoe store, for example. The foot length information management system 10 manages information regarding customers' foot length measured in a store. The foot length information management system 10 also notifies a customer of a replacement time for shoes or of information regarding optimum shoes, based on foot length information 35. Further, the foot length information management system 10 manages information regarding human foot length, thereby estimating a size variation to notify a customer of a replacement time for shoes. In the following embodiment, a system for managing children's foot length, of which the growth is significantly remarkable, will be described as an example.

Figure 1:
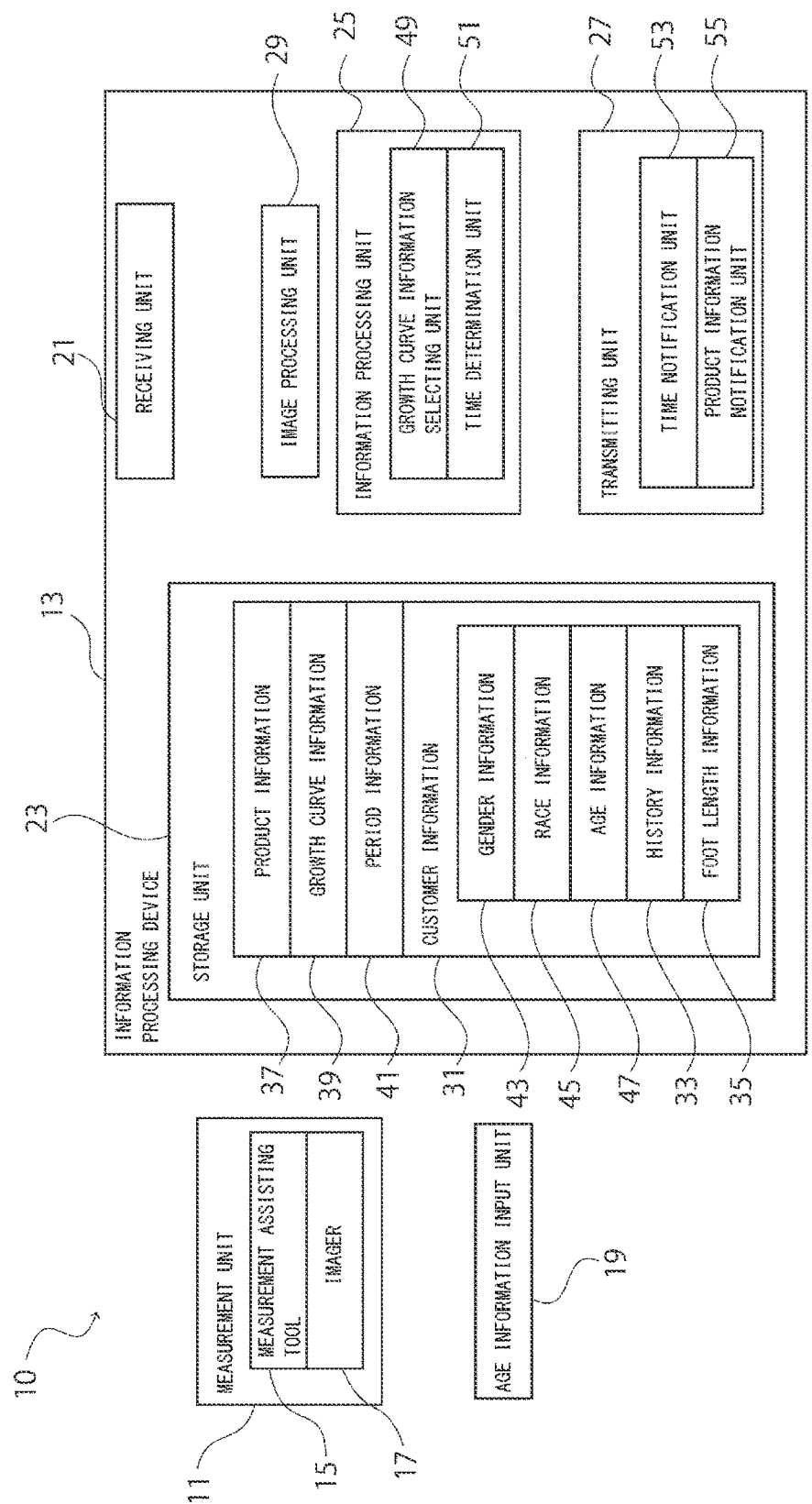
FIG. 1 is a block diagram of a foot length information management system according to an embodiment.

FIG. 1 is a block diagram of the foot length information management system. As shown in FIG. 1, the foot length information management system 10 includes a measurement unit 11 that measures foot length, and an information processing device 13 that processes information obtained by the measurement unit 11. The measurement unit 11 may be placed in a store, for example. A salesperson measures the foot length of a customer using the measurement unit 11. The foot length information 35 obtained by the measurement unit 11 is managed by the information processing device 13. Based on the foot length information 35, for example, the information processing device 13 calculates an optimum replacement time for shoes appropriately for the growth of a child and notifies a customer of the replacement time. The customers as used herein include children whose foot length has been measured, and their guardians, for example. The information processing device 13 may be placed in a store, or may be placed remotely from a store so that pieces of information obtained in multiple stores can be collectively processed.

The measurement unit 11 may have any configuration as long as it is configured to notify the information processing device 13 of the foot length information 35 of a child. An example of the measurement unit 11 may be a calibrated measurement tool. A salesperson measures the foot length of a child using the calibrated measurement tool. The salesperson then enters information regarding the foot length of the child into the information processing device 13. The information processing device 13 may manage the foot length information 35 of customers measured with such a calibrated measurement tool.

In the illustrated example, the measurement unit 11 includes a measurement assisting tool 15 that assists in measuring children's foot length, and an imager 17, such as a camera. The measurement assisting tool 15 is a member having a standardized length, for example. A salesperson places the measurement assisting tool 15 beside a foot of a customer and captures an image of the state by means of the imager 17. At the time, the salesperson captures an image of at least the customer's tiptoe and at least part of the measurement assisting tool 15. This generates an image in which the position of the tiptoe with respect to the standardized measurement assisting tool 15 can be found. Accordingly, when the length of the measurement assisting tool 15 is known, the customer's foot length can be obtained. The image captured by the measurement unit 11 is transmitted to the information processing device 13.

The foot length information management system 10 includes an age information input unit 19. The age information input unit 19 is an input interface, such as a keyboard and a touch screen, and is placed together with the measurement unit 11 in a store. When the foot length of a customer is measured by means of the measurement unit 11, the age information input unit 19 is used to enter age information 47 of the customer. The age information 47 thus entered is transmitted to the information processing device 13.

The information processing device 13 mainly includes a receiving unit 21 through which information is received, a storage unit 23 that stores information, and an information processing unit 25 that performs information processing based on received information, for example. When information needs to be transmitted from the foot length information management system 10 to customers, a transmitting unit 27, through which information is transmitted to a customer, is provided in the information processing device 13. Also, when the measurement unit 11 includes the measurement assisting tool 15, an image processing unit 29, which processes an image obtained from the measurement unit 11, is provided in the information processing device 13.

The receiving unit 21 may be an input port connected to a communications network, for example, and various pieces of information are received from outside the information processing device 13 through the receiving unit 21. Information received through the receiving unit 21 is stored in the storage unit 23, provided to the image processing unit 29, or provided to the information processing unit 25, depending on the kind of information. Particularly, when customer information 31 is received through the receiving unit 21, the information is stored as customer information 31 in the storage unit 23. Information to be stored in the storage unit 23 includes the customer information 31 regarding a new customer, history information 33 obtained when a customer purchases shoes, and the foot length information 35 obtained when shoes are purchased and foot length is measured, for example.

The storage unit 23 may be constituted by a storage medium, such as non-volatile memory. The storage unit 23 stores various pieces of information used when the information processing device 13 manages the foot length information 35 or determines a replacement time for shoes, for example. The storage unit 23 stores product information 37, growth curve information 39, and the customer information 31. The storage unit 23 may also store period information 41.

The product information 37 is information regarding products, such as information regarding the types of shoes sold in a store or an affiliated store, information regarding stocks, and information regarding the sizes of shoes in stock.

Figure 2:
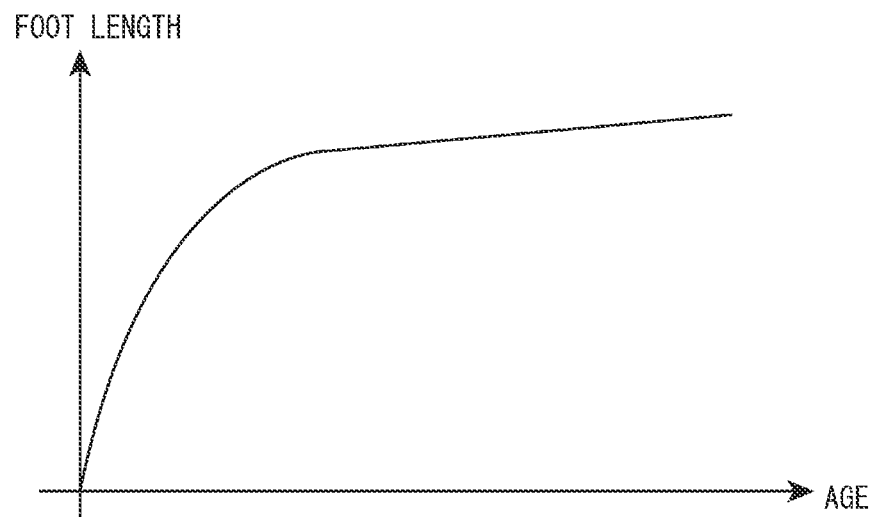
FIG. 2 shows an example of a growth curve.

The growth curve information 39 is information regarding multiple patterns of growth curves. The foot length of a child changes with age but does not grow arithmetically. FIG. 2 shows an example of a growth curve. As shown in FIG. 2, the growth of child's foot length tends to be large in early childhood and decrease with age thereafter. A growth curve is a curve obtained by performing statistical processing on information obtained by measuring such changes in foot length with time of a number of children. There are multiple types of growth curve information 39 prepared. The growth curve information 39 may be managed based on genders and races. Also, the growth curve information 39 may be updated based on the foot length information 35 obtained by the measurement unit 11.

Referring back to FIG. 1, the period information 41 is information including a child's age and a replacement period for shoes related to each other. The period information 41 is obtained by performing statistical processing on information including children's ages, growth of foot length, and shoe sizes. For example, it is assumed here that a statistical result shows that the shoe size of a child between the age of 0 and 3 is increased by one every three months, and the shoe size of a child aged 3 years or over is increased by one every six months. In this case, the period information 41 will include information indicating that the replacement period for shoes of customers between the age of 0 and 3 is three months, and the replacement period for shoes of customers aged 3 years or over is six months. The period information 41 can be used solely, and the information processing device 13 may refer to the period information 41 to notify a customer of a replacement time based on the period specified in the period information 41.

The customer information 31 includes gender information 43, race information 45, and the age information 47 of a customer, the history information 33 regarding the customer's purchase history, and the foot length information 35 of the customer measured in the past. The gender information 43 and other various pieces of information in the customer information 31 are related to information for identifying a customer, such as the name and a membership number of the customer.

The image processing unit 29 is provided when the measurement unit 11 includes the measurement assisting tool 15 and the imager 17. The image processing unit 29 analyzes image information, received through the receiving unit 21, of an image captured by the imager 17 to determine the foot length. The image processing unit 29 analyzes image information received through the receiving unit 21 to determine the foot length of a customer based on a relative positional relationship between the measurement assisting tool 15 and the customer's tiptoe. The foot length thus determined by the image processing unit 29 is used as the foot length information 35 by the information processing unit 25 to perform various processes. Also, the foot length information 35 may be stored as the customer information 31 in the storage unit 23. The image processing unit 29 functions together with the measurement unit 11 to measure the foot length of a customer, and can be substantially regarded as part of the measurement unit 11, even when the image processing unit 29 is located at a remote place. Also, the image processing unit 29 may be physically included within the measurement unit 11, or may be physically separated from the measurement unit 11 but placed in a store where the measurement unit 11 is placed.

The information processing unit 25 performs various processes based on the information received through the receiving unit 21, the information stored in the storage unit 23, and the information processed by the image processing unit 29. More specifically, the information processing unit 25 writes received information into the storage unit 23, retrieves necessary information from the storage unit 23, and transmits various information to a customer via the transmitting unit 27. The information processing unit 25 also selects a growth curve appropriate for a customer to determine a replacement time for shoes of the customer. The information processing unit 25 mainly includes a growth curve information selecting unit 49 that selects a growth curve, and a time determination unit 51 that determines a replacement time. Also, the information processing unit 25 may update the age information 47 of a customer, as needed.

The growth curve information selecting unit 49 selects a growth curve appropriate for a customer, based on the foot length information 35 generated in the image processing unit 29, the growth curve information 39, and the age information 47 entered into the age information input unit 19. For example, the growth curve information selecting unit 49 refers to the foot length information 35 and the age information 47 to select a growth curve that satisfies both the foot length and age conditions. More specifically, the growth curve information selecting unit 49 selects the growth curve information 39 that includes a curve appropriate for both the age and the foot length, among growth curves of which an example is shown in FIG. 2. When there are multiple pieces of growth curve information 39 that satisfy the conditions, all the pieces of growth curve information 39 satisfying the conditions may be selected. When multiple pieces of growth curve information 39 are selected, a request for other information (the race, gender, or the like) of the customer may be further made to a salesperson, for example, so as to narrow down the growth curve information 39. The growth curve information selecting unit 49 may relate the growth curve information 39 thus selected to the customer information 31 and write the information as the customer information 31 into the storage unit 23. When the customer information 31 includes the foot length information 35, past foot length information 35 may also be referred to, and the growth curves may be narrowed down by finding a growth curve appropriate for the past foot length information 35 (and the age information 47 at the time of acquisition of the foot length information 35), the foot length information 35 measured by the measurement unit 11, and the customer's current age.

The time determination unit 51 determines a purchase time for the next shoes based on the customer information 31 and the growth curve information 39 related to the customer information 31. For example, on a related growth curve, the time determination unit 51 plots the size of shoes currently used by a customer based on the history information 33 of the customer, or plots the foot length information 35 of the customer. The time determination unit 51 then determines a time when the foot length of the customer matches the next shoe size, based on the growth curve information 39. When multiple growth curves are related to the customer, purchase times for shoes may be derived based on the multiple growth curves. Among the derived purchase times, the earliest purchase time or an intermediate time between an early time and a late time may be set as the purchase time, for example. The purchase time determined by the time determination unit 51 is transmitted to the customer via the transmitting unit 27.

The time determination unit 51 may also refer to the purchase history and the age information 47 to determine a purchase time, which is different from the purchase time determined using a growth curve. For example, shoes of infants, who often play in parks or the like, may be abraded or damaged earlier than the time when the sizes of the shoes do not fit because of the growth of the infants. Accordingly, the time determination unit 51 may determine a scheduled purchase time, irrespective of the growth curves, based on the customer's age, for example. The two kinds of purchase times may be determined in parallel, upon request from the customer, for example.

The transmitting unit 27 may be an output port connected to a communications network, for example, and various pieces of information are transmitted to outside the information processing device 13 through the transmitting unit 27. The transmitting unit 27 includes a time notification unit 53 that notifies a customer of a time determined by the time determination unit 51, and a product information notification unit 55 that transmits the product information 37 to a customer.

The time notification unit 53 notifies a customer of a purchase time determined by the time determination unit 51, by means of an e-mail, chatting, a social networking service, and an automatic voice call, for example. The time notification unit 53 may notify a customer of a purchase time at any time, such as when the history information 33 of the customer is updated and a time around the purchase time. The time of notification may be appropriately changed upon request from the customer.

The product information notification unit 55 notifies a customer of the product information 37 by means of an e-mail, chatting, a social networking service, and an automatic voice call, for example. The notification by the product information notification unit 55 may be performed together with the notification by the time notification unit 53, or may be performed when a new product is arrived and the product information 37 is updated, for example. The product information notification unit 55 may refer to the history information 33 of customers, the growth curve information 39 related to the customers, and the product information 37, so as to transmit, to a customer for whom a purchase time is approaching, the product information 37 regarding products that come in sizes suitable for the customer, for example.

There will now be described the operation of the foot length information management system 10. When a customer comes to purchase shoes, a salesperson in the store obtains information regarding the customer's foot length, such as a captured image, using the measurement unit 11. When the customer information 31 of the customer has been registered, the salesperson may obtain the identification information of the customer. For a new customer, the salesperson may obtain the customer information 31, including the age, gender, and race. The information regarding foot length and the customer information 31 obtained by the salesperson is transmitted to the information processing device 13.

The information processing device 13 analyzes the information regarding foot length, and the image processing unit 29 determines the foot length, if necessary. The foot length information 35 and the received customer information 31 is stored as the customer information 31 in the storage unit 23. For the customer information 31 of a new customer, the customer information 31 and the foot length information 35 is related to each other and stored. When the customer information 31 has been already registered, the foot length information 35 newly obtained is related to the age and stored, without deleting the previous foot length information 35. Also, when the customer has purchased shoes in the store, the size of the purchased shoes or the like is stored as the history information 33 in the storage unit 23.

The growth curve information selecting unit 49 refers to the customer information 31 at an arbitrary time to select a growth curve appropriate for the customer. For a new customer, a growth curve appropriate for the foot length and the age of the customer is selected from among multiple pieces of growth curve information 39. The selected growth curve is related to the customer information 31 and stored in the storage unit 23. Also, when the foot length information 35 of a customer whose customer information 31 has been registered is recorded, the related growth curve information 39 may be updated. In this case, a growth curve appropriate for the customer can be selected by referring to the history of the foot length information 35.

Through such processing, the growth curve information 39 appropriate for each customer is related to the customer and managed. The managed information may be used when the growth curve information 39 is generated with the approval of the customer, or may be used as reference information for new product development, for example. The managed information may also be used to notify the customer of a purchase time for next shoes.

The time determination unit 51 determines a purchase time for next shoes of a customer based on a growth curve and the foot length information 35, at an arbitrary time after the foot length information 35 is registered or updated, for example. When a purchase time for next shoes is determined, the product information 37 may be referred to so that the sizes of the products can be considered. The time notification unit 53 notifies the customer of a replacement time at an arbitrary time, such as when the purchase time is approaching.

Even after the growth of the customer's foot length is reduced, the time determination unit 51 may continuously determine a replacement time based on a growth curve. In this case, the time determination unit 51 and the time notification unit 53 may set, as a replacement time, a period for which shoes are presumably worn, and may notify the customer of the replacement time after the replacement time, for example. In this case, since the frequency of notification of a replacement time is reduced, the product information notification unit 55 may solely notify the customer of the product information 37, separately from the notification by the time notification unit 53. When the foot length information is not updated after the period for which shoes are presumably worn has elapsed, the foot length information management system 10 may send a notification for prompting the customer to measure the foot length, for example.

Through such a series of processes, the customer can recognize a replacement time for shoes, without managing the replacement times for shoes by himself or herself. Particularly, when a guardian determines the replacement times for shoes of his or her child, replacement of shoes can be prompted at an appropriate time, without relying on the child's subjective judgment.

There will now be detailed an embodiment relating to a measurement assisting tool. In the following, two examples of the measurement assisting tool are described, but the measurement assisting tool 15 of the foot length information management system is not limited to the two examples.

Figure 3:
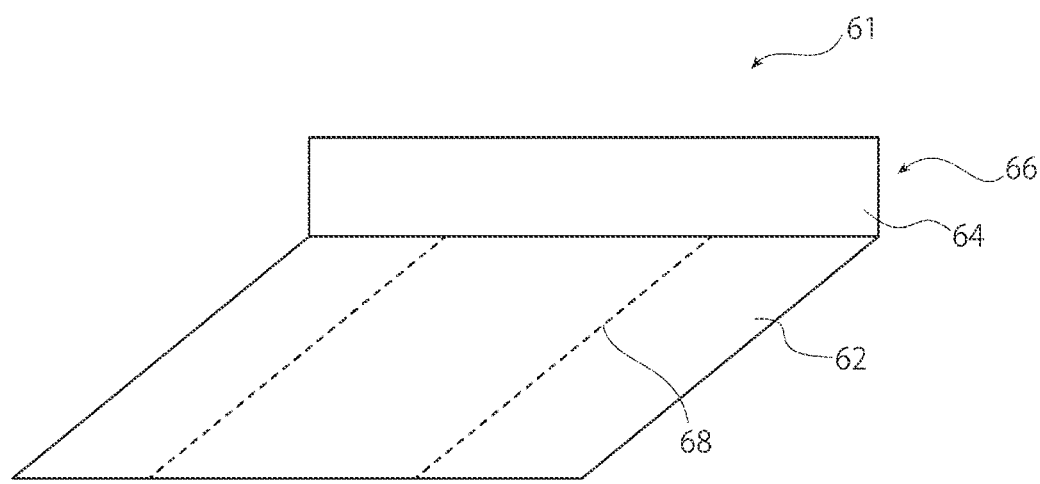
FIG. 3 shows a measuring board as an example of a measurement assisting tool.

FIG. 3 shows a measuring board as an example of the measurement assisting tool. A measuring board 61 includes a main body 66, which includes a placement part 62 on which a foot is placed, and a wall part 64 used to position the foot. The main body 66 may be suitably formed by folding a sheet of board into a predetermined shape. The main body 66 may be suitably made of paper that is sufficiently thick and foldable, such as corrugated cardboard. Parts of the main body 66, including the placement part 62 and the wall part 64, are formed by assembling a sheet of paper cut out into a predetermined shape. The main body 66 may be formed by opening and flattening a shoebox. On the upper surface of the placement part 62, measurement markers 68 are provided. For measurement, the foot length can be measured using the measurement markers 68. Instead of the measurement markers 68, a calibration mark of a predetermined shape may be used. In this case, the foot length may be obtained by capturing an image of a foot together with the calibration mark and analyzing the captured image. An example of such a measuring board is described in the international application PCT/JP2019/028147, and the measuring board described therein may also be included as the measurement unit.

Another embodiment relating to a measurement assisting tool will now be detailed. The measurement assisting tool described below is particularly suitable for measurement of children's foot length. Conventionally, to measure the foot length of a child, the child is led onto a measurement device provided with scale marks, for example, and needs to keep standing on the measurement device until the measurement is completed. Also, during measurement, the child's foot needs to be maintained parallel with the direction in which the scale marks are arranged, and the child needs to maintain the posture.

However, when the measurement device is a large-scale device, children may be sometimes unable to gain a sense of safety. Also, a conventional measurement device requires a child to maintain an appropriate posture for a long time. Similar problems may arise when the subject of measurement is an elderly person or a person in poor health.

With the measurement assisting tool, on the other hand, children can gain a sense of safety, and the foot length of a child can be measured without requiring the child to maintain an appropriate posture for a long time. In the following, the measurement assisting tool will be detailed.

Figure 4:
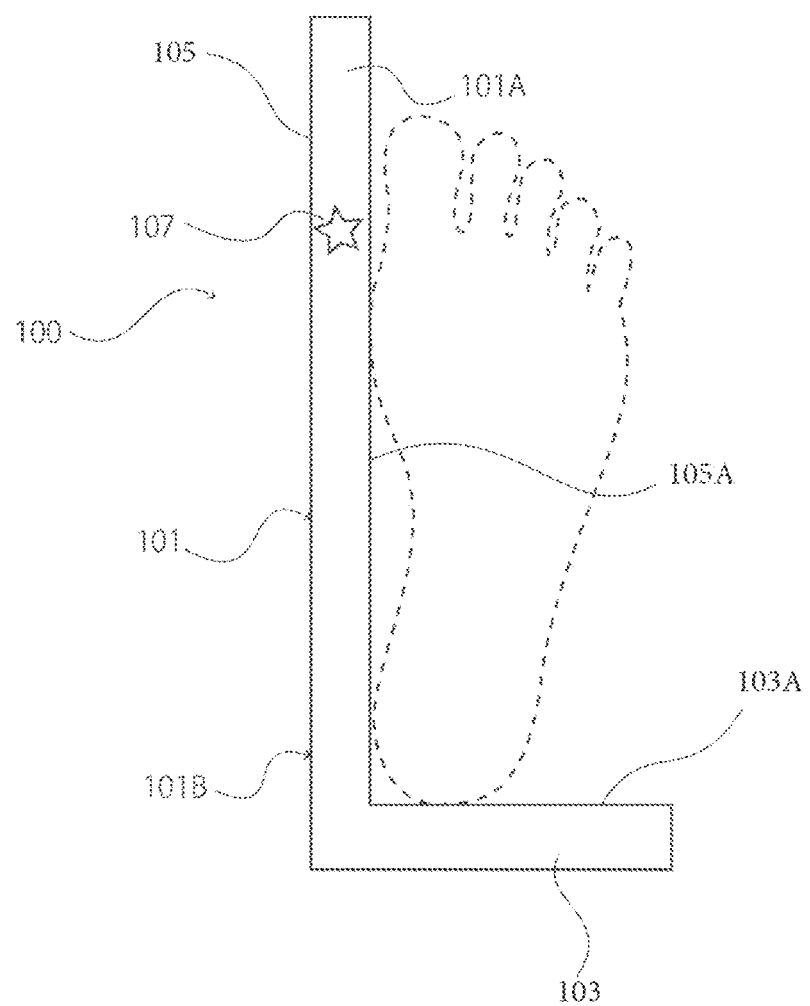
FIG. 4 is a top view of a measurement assisting tool according to the embodiment.

FIG. 4 is a top view of a measurement assisting tool 100. The measurement assisting tool 100 is placed on a surface, such as a floor on which a child is standing, and can be freely moved on the surface without moving the child. Thus, in the case of a conventional measurement device, a child needs to be led onto the measurement device, whereas the measurement assisting tool 100 can be moved to a position where a child is standing.

As shown in FIG. 4, the measurement assisting tool 100 includes a main body 101 of an L shape. The main body 101 has a three dimensional shape made by thickening the L shape overall. Accordingly, each of an upper surface 101A and a bottom surface 101B of the main body 101 has an L shape. The thickness of the main body 101 is determined in consideration of the height from the floor surface on which a child is standing to the rearmost part of a heel of the child. More specifically, the main body 101 has a thickness of 2.5-4 cm, which is considered to be a thickness such that the main body 101 placed on the floor surface is in contact with the rearmost part of a child's heel.

The main body 101 is configured by connecting an end part of an elongate first member 103 and an end part of an elongate second member 105 such that the members make a right angle. The length in an axial direction of the second member 105 is longer than that of the first member 103. The thickness dimension described above is only applied to the first member 103, which is brought into contact with a heel, and the thickness of the second member 105 is not particularly limited. Accordingly, a material thinner than that of the first member 103 may be used for the second member 105. The upper surface 101A and the bottom surface 101B of the main body 101 are parallel to each other. The main body 101 may be made of any material, such as wood and plastic. Also, a rubber or fiber sheet may be pasted over the bottom surface 101B of the main body 101 for non-slip processing. Wood may be suitably used to provide a sense of safety to children. The length in an axial direction of the first member 103 may be any length, as long as it is longer than an average foot width of children. Also, an area for providing an indication of a part with which a heel is brought into contact may be specified near the middle of the first member 103. There are various ways of specifying the area, such as coloring a certain range and providing a curved recess into which a heel fits. The length in an axial direction of the second member 105 may be at least 15 cm. If the second member 105 is shorter than foot length, the foot length cannot be measured accurately. At least inner side surfaces 103A and 105A of the first member 103 and second member 105 are made flat and respectively extend parallel with the axes of the members.

The main body 101 is not provided with a measurement means, such as a scale. On the upper surface 101A of the second member 105, a calibration mark 107 is provided as a reference for image capturing. The calibration mark 107 is used in analysis of a captured image to calculate the number of pixels of the captured image, a relative relationship between an actual size and a size in the captured image, or the like, or to perform parallel correction for the orientation of the image. The calibration mark 107 may have any shape, such as a character, a figure, or a combination thereof. The calibration mark 107 may suitably have a shape that is not symmetrical with respect to the axis of the second member 105. Also, the calibration mark 107 may suitably be provided closer to the tip of the second member 105, or closer to one end of the second member 105 located opposite to the other end connected to the first member 103. More specifically, the calibration mark 107 is provided closer to the tip of the second member 105, with respect to the middle of the length in an axial direction of the second member 105. In the main body 101, at least the color of the second member 105 may suitably be different from the colors of bare feet. More suitably, the color of the second member 105 may be one of the non-mixed colors expressed in the RGB system (R255: G0:B0, R0:G255:B0, or R0:G0:B255). On the other hand, the color of the calibration mark 107 may suitably be white (R255:G255:B255), which is the color furthest from the nonmixed colors, among colors expressed in the RGB system. Although the details will be described later, the second member 105 and the calibration mark 107 having such colors can improve the detection accuracy of the calibration mark 107 when image processing on a captured image of the measurement assisting tool 100 is performed.

When the measurement assisting tool 100 is to be used, a salesperson may get closer to a position where a barefoot child is standing and bring the measurement assisting tool 100 placed on the floor surface into contact with a foot of the child, for example. At the time, the child may stand on a soft mat. In this case, the color of the mat may suitably be different from the colors of the bare feet and socks. Also, the color of the mat may be different from the color of the calibration mark 107. The measurement assisting tool 100 is moved such that the inner side surface 103A of the first member 103 is in contact with the heel of the child and the inner side surface 105A of the second member 105 is in contact with the thenar of the child, as shown in FIG. 4. The salesperson then captures an image of the foot and the measurement assisting tool 100 such that the image includes at least the tiptoe and the calibration mark 107. For the image capturing, a simple imaging device, such as a smartphone, may be used. Thereafter, the salesperson transmits the captured image to the image processing unit 29. Also, image processing may be performed using a dedicated application on the smartphone. In this case, the captured image need not be transmitted.

The image processing unit 29 performs calibration for the color, position, size, orientation, and the like using the calibration mark 107, and measures the distance between the tip of the second member 105 and the tiptoe (in an axial direction of the second member 105). The image processing unit 29 retains information on the distance between the inner side surface 103A of the first member 103 and the tip position of the second member 105 (in an axial direction of the second member 105). The image processing unit 29 calculates the foot length by subtracting the distance between the tip of the second member 105 and the tiptoe, from the distance between the inner side surface 103A of the first member 103 and the tip position of the second member 105.

Although the foot length of a right foot is measured in the abovementioned example, when the foot length of a left foot is measured, another measurement assisting tool 100 having a symmetrical shape of the abovementioned measurement assisting tool 100 may be prepared, or the abovementioned measurement assisting tool 100 may be placed top side down. In this case, the calibration mark 107 may be also provided on the bottom surface 101B of the measurement assisting tool 100.

With the measurement assisting tool 100, irrespective of the position or posture of a standing child, the foot length of the child can be easily measured without moving the child. Also, since the foot length is measured by performing image processing using an imaging device, the time for which the child needs to stand still is substantially only the moment of image capturing.

The measurement assisting tool 100 may be used together with the foot length information management system 10, or may be used separately.

Figure 5:
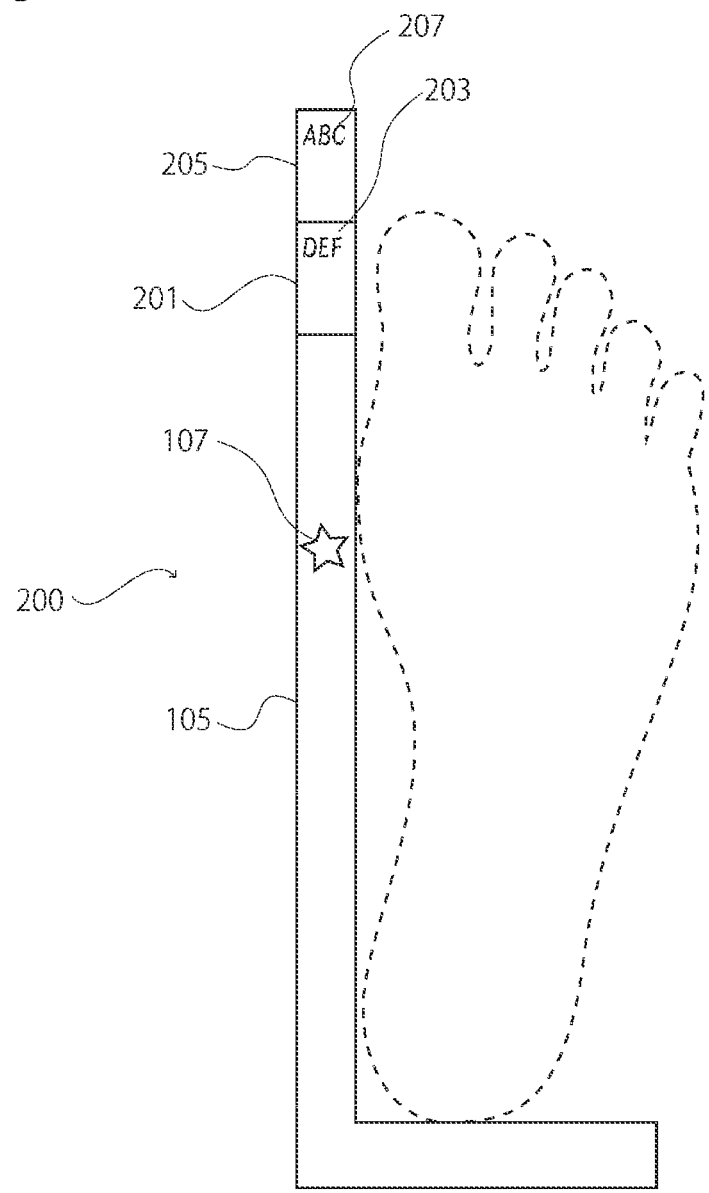
FIG. 5 is a top view of a measurement assisting tool according to a modification.

FIG. 5 shows a modification of the measurement assisting tool. The second member 105 is provided with the calibration mark 107, and the tip of the second member 105 is located at a certain distance from the inner side surface 103A of the first member 103. Meanwhile, children's foot length varies in a range from 8 cm to 25 cm, for example, depending on the age. Accordingly, when foot length of children of all ages is to be measured using a single measurement assisting tool 100, a large measurement assisting tool 100 needs to be used for measurement, even for children with shorter foot length.

To solve such a problem, a measurement assisting tool 200 according to a modification includes at least one extension member 201 of which the shape of a cross section is identical with that of the second member 105. The extension member 201 is connectable to the tip of the second member 105, and an additional calibration mark 203 is provided on the upper surface 101A of the extension member 201. Also, at the tip of the extension member 201, another extension member 205 may be provided. The additional extension member 205 is connected to the tip of the extension member 201, and a calibration mark 207 is provided on the upper surface 101A of the extension member 205. For connection between the second member 105 and the extension members 201 and 205, any connection method may be used. For example, the second member 105 and the extension members 201 and 205 may be connected using a combination of projections and fitting holes, magnets, or the like. In this case, the extension members 201 and 205 may suitably be configured such that they can be connected only in a predetermined order. For example, the shapes of the projections and fitting holes at the connection parts may be made different, or the magnetic properties of the magnets may be made different, so that the secondary extension member 205 cannot be directly connected to the second member 105. Also, the color of each of the extension members 201 and 205 may be made different from the color of the second member 105. When the colors of the extension members 201 and 205 are stored in advance in the image processing unit 29, the image processing unit 29 can clearly recognize whether the extension member 201 or 205 is connected to the second member 105 and, if connected, the image processing unit 29 can also clearly recognize which of the extension members 201 and 205 is connected. In these cases, the image processing unit 29 calculates the foot length based on the distance between the inner side surface 103A of the first member 103 and the tip of the extension member 201 or 205.

The additional calibration marks 203 and 207 are marks different from each other, and may also be different from the calibration mark 107 of the second member 105. The three calibration marks 107, 203, and 207 may have the same shape, but, in this case, the orientations or colors of the marks may suitably be different such that the image processing unit 29 can distinguish among the marks. When the shapes of all the calibration marks 107, 203, and 207 are made different, the image processing unit 29 can distinguish among the calibration mark 107 and the additional calibration marks 203 and 207. The extension member 201 is separated from the second member 105, and may be attachable to and detachable from the tip of the second member 105.

When measurement is performed with the extension members 201 and 205 connected, the image processing unit 29 may be notified of the number of extension members used by the measurer. Also with such a configuration, the image processing unit 29 can recognize which member has the tip part shown in an image. Also, all the calibration marks 107, 203, and 207 may be made different such that the image processing unit 29 can recognize which member has the tip part shown in an image by the mark. Also, the photographer may be requested to include all the calibration marks 107, 203, and 207 in the image to be captured, so that the image processing unit 29 can recognize which member has the tip part shown in the image, based on the number of calibration marks 107, 203, and 207 shown in the image.

Figure 6:
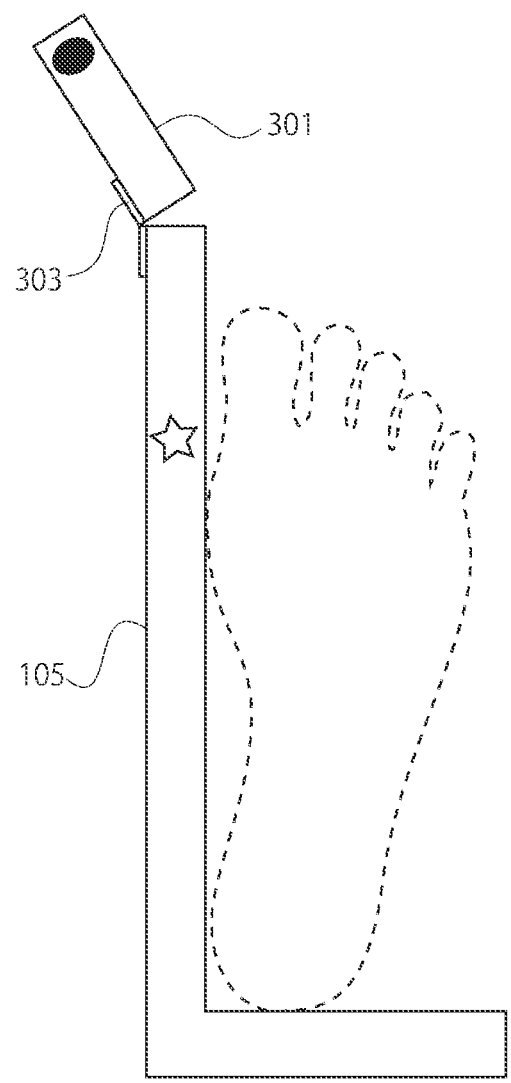
FIG. 6 is a top view of a measurement assisting tool according to another modification.

FIG. 6 shows a measurement assisting tool according to another modification. In the example of FIG. 6, an extension unit 301 is connected to the tip of the second member 105 by means of a hinge 303. The hinge 303 is fixed to each of an outer side surface of the extension unit 301 and an outer side surface of the second member 105. Therefore, when the extension unit 301 is not used, the extension unit 301 can be folded over on the outer side. In addition, since the extension unit 301 and the second member 105 are integrally structured, the loss of the extension unit 301 can be prevented.

The present invention is not limited to the aforementioned embodiment and modifications, and further modifications may be appropriately made to each configuration without departing from the technical scope of the invention as described in the claims. Although a system for managing children's foot length is described as an example in the aforementioned embodiment, growth curves for adults may be prepared and used. Particularly, since elderly persons' foot length tends to change, managing the foot length using the foot length information management system will be advantageous.

INDUSTRIAL APPLICABILITY

The present invention is industrially applicable in the fields of foot length information management systems, systems for determining replacement times for shoes, and measurement assisting tools.

REFERENCE SIGNS LIST

10 foot length information management system
11 measurement unit
13 information processing device
15 measurement assisting tool
17 imager
19 age information input unit
25 information processing unit
29 image processing unit
49 growth curve information selecting unit
51 time determination unit
53 time notification unit
55 product information notification unit
100 measurement assisting tool
101 main body
101A upper surface
101B bottom surface
103 first member
105 second member
107 calibration mark
201 extension member
203 calibration mark

The invention claimed is:

1. A measurement assisting tool movable on a placement surface on which a foot is placed, the measurement assisting tool comprising:
    an L-shaped main body that includes i) a first member, ii) a second member extending perpendicular from one end of the first member to form an L shape, iii) an L-shaped bottom surface to be in contact with the placement surface, and iv) an L-shaped upper surface facing a side opposite to the L-shaped bottom surface; and
    a calibration mark provided on the L-shaped upper surface,
    wherein the second member is longer than the first member,
    wherein, when the measurement assisting tool is in use, the first member is configured to be arranged at a heel of a user while the second member is configured to be arranged at a thenar of the user, and
    wherein the calibration mark has an asymmetrical shape with respect to a longitudinal axis of the second member.

2. The measurement assisting tool according to claim 1, wherein
    the second member includes i) a first end connected to the one end of the first member and ii) a second end opposite the first end, and
    the calibration mark is provided closer to the second end of the second member than to the first end of the second member.

3. The measurement assisting tool according to claim 2, further comprising an extension member connected to the second end of the second member and extending in the same direction as the second member, wherein
an additional calibration mark is provided on an upper surface of the extension member.

\* \* \* \* \*